United States Patent
Qian et al.

(10) Patent No.: US 7,776,362 B2
(45) Date of Patent: Aug. 17, 2010

(54) FORMULATIONS FOR THE DECONTAMINATION OF TOXIC CHEMICALS

(75) Inventors: Jianquo Qian, St. Louis, MO (US); W. Ron Purdum, Maryland Heights, MO (US)

(73) Assignee: Clean Earth Technologies, LLC, Earth City, MO (US)

( * ) Notice: Subject to any disclaimer, the term of this patent is extended or adjusted under 35 U.S.C. 154(b) by 731 days.

(21) Appl. No.: 11/329,531

(22) Filed: Jan. 11, 2006

(65) Prior Publication Data

US 2006/0204590 A1 Sep. 14, 2006

Related U.S. Application Data

(60) Provisional application No. 60/642,964, filed on Jan. 11, 2005.

(51) Int. Cl.
*A01N 39/00* (2006.01)

(52) U.S. Cl. .................... 424/616; 510/110; 588/313

(58) Field of Classification Search ............. 510/224, 510/302, 312, 372, 375, 382, 406, 642; 588/300, 588/313; 424/616
See application file for complete search history.

(56) References Cited

U.S. PATENT DOCUMENTS

| | | | |
|---|---|---|---|
| 3,968,048 A * | 7/1976 | Bolan ......................... 510/196 |
| 3,992,333 A | 11/1976 | Emmons et al. |
| 4,146,368 A | 3/1979 | Troffkin et al. |
| 4,708,869 A | 11/1987 | Koblin |
| 4,744,917 A | 5/1988 | Scardera et al. |
| 4,850,729 A | 7/1989 | Kramer et al. |
| 4,883,608 A | 11/1989 | Trujillo et al. |
| 5,078,896 A | 1/1992 | Rorig et al. |
| 5,322,644 A | 6/1994 | Dunn et al. |
| 5,421,906 A | 6/1995 | Borah |
| 5,584,071 A | 12/1996 | Kalyon et al. |
| 5,723,095 A * | 3/1998 | Fricker et al. ................ 422/292 |
| 5,760,089 A | 6/1998 | Cronce |
| 6,110,883 A * | 8/2000 | Petri et al. ................... 510/372 |
| 6,143,088 A | 11/2000 | Lion et al. |
| RE37,207 E | 6/2001 | Cronce |
| 6,245,957 B1 | 6/2001 | Wagner et al. |
| 6,369,288 B1 | 4/2002 | Brown |
| 6,417,151 B1 * | 7/2002 | Grothus et al. .............. 510/312 |
| 6,525,237 B1 | 2/2003 | Purdon et al. |

(Continued)

FOREIGN PATENT DOCUMENTS

WO WO03/028429 A2 4/2003

OTHER PUBLICATIONS

Patai, S.,"The Chemistry of Peroxides", John Wiley and Sons, New York, 1983, p. 287-299.

(Continued)

*Primary Examiner*—Timothy C Vanoy
*Assistant Examiner*—Richard M Rump
(74) *Attorney, Agent, or Firm*—Grant D. Kang; Kang Intellectual Property Law, LLC

(57) ABSTRACT

A decontaminant composition comprising a peroxide; an organic co-solvent; an amine, which in reaction with the peroxide is a source of a perhydrolysis species; a phase transfer catalyst comprising at least one quaternary ammonium compound; a metal oxide catalyst; a chemical base; and at least one pH buffering compound.

23 Claims, 7 Drawing Sheets

The Relationship between pH and NaOH/Hydrogen Peroxide

U.S. PATENT DOCUMENTS

| | | | |
|---|---|---|---|
| 6,537,382 B1 | 3/2003 | Bartram et al. | |
| 6,553,887 B1 | 4/2003 | Bureaux et al. | |
| 6,566,574 B1 | 5/2003 | Tadros et al. | |
| 6,569,353 B1* | 5/2003 | Giletto et al. | 252/186.28 |
| 6,630,105 B1 | 10/2003 | O'Neill et al. | |
| 6,723,890 B2 | 4/2004 | Tucker et al. | |
| 6,723,891 B1* | 4/2004 | Wagner et al. | 588/316 |
| 6,790,817 B2* | 9/2004 | Gladfelter et al. | 510/224 |
| 2003/0100465 A1* | 5/2003 | Kilkenny et al. | 510/384 |
| 2003/0171239 A1* | 9/2003 | Patel et al. | 510/406 |
| 2005/0282722 A1* | 12/2005 | McReynolds et al. | 510/302 |
| 2006/0199752 A1* | 9/2006 | Tichy et al. | 510/375 |
| 2006/0229225 A1* | 10/2006 | Martin et al. | 510/375 |

OTHER PUBLICATIONS

"Decontamination Effectiveness of the Electrostatic Decontamination System Technology", Clean Earth Technologies, LLC, 2004.

Epstein, J. et al., "Reaction of Paraoxon with Hydrogen Peroxide in Dilute Aqueous Solution", *Journal of Organic Chemistry*, vol. 21, pp. 796-797.

Modec, I., "An Enhanced Formulation for Decontamination and Mitigation of CBW Agents and Biological Pathogens", *MDF-200*, 2003.

Munro, N.B., et al., "The Sources, Fate, and Toxicity of Chemical Warfare Agent Degradation Products", *Environmental Health Perspectives*, 1999, vol. 107, pp. 933-974.

Wagner, G.W. et al., Decon Green, U.S. Army Edgewood Chemical Biological Center, 2004.

Wagner, G.W. et al., "Rapid Nucleophilic/Oxidative Decontamination of Chemical Warfare Agents", *Ing. Eng. Chem. Res.*, 2002, vol. 41, pp. 1925-1928.

Yang, Y.C. et al., "Decontamination of Chemical Warfare Agents", *Chemical Reviews*, 1992, vol. 92, pp. 1729-1743.

Yang, Y.C. et al., "Kinetics and Mechanism of the Hydrolysis of 2-Chloroethyl Sulfides", *Journal of Organic Chemistry*, vol. 53, pp. 3293-3297.

Yang, Y.C., "Chemical Reactions for Neutralizing Chemical Warfare Agents", *Chem. Ind.*, 1995, vol. 9, pp. 334-337.

Wagner, G.W. et al. "Molybdate/Peroxide Oxidation of Mustard in Microemulsions", *Langmuir*, 2001, vol. 17, pp. 4809-4811.

Yang, Y.C., "Perhydrolysis of Nerve Agent VX", *J. Org. Chem.*, 1993, vol. 58, pp. 6964-6965.

Yang, Y.C., "Peroxyhydrolysis of Nerve Agent VX and Model Compounds and Related Nucleophilic Reacations", *J. Chem. Soc., Perkin Trans.*, 1997, vol. 2, pp. 607-613.

Hsu, F.L., "Reactions of N-Ethyl-(HN-1), N-Methyl-Bis(2-chloroethyl)Amine (HN-2), and Tris(20Chloroethyl)Amine (HN-3) with Peroxides", *Edgewood Chemical Biological Center*, Report No. ECBC-TR-071, 2000.

Hale, M.L., "Microtiter-Based Assay for Evaluating the Biological Activity of Ribosome-Inactivating Proteins", *Pharmacology & Toxicology*, 2001, vol. 88, pp. 255-260.

Drago, et al., "Catalytic Activation of Hydrogen Peroxide—A Green Oxidant System", *ERDEC Scientific Conference on Chemical and Biological Defense Research*, 1997, pp. 341-342.

\* cited by examiner

Figure 1. The Relationship between pH and NaOH/Hydrogen Peroxide

Figure 2. The Relationship between pH and NH4OH/Hydrogen Peroxide ately 1:1 on a volumetric basis, followed by the addition of a small amount of a third part that contains the metal oxide catalyst and the phosphonate sequestering agent in a water solution. The Mo as MoO$_4^=$ should be in the concentration range 1-4 mM in the final mixed
FORMULATIONS FOR THE DECONTAMINATION OF TOXIC CHEMICALS

CROSS REFERENCE TO RELATED APPLICATIONS

This application claims the benefit of U.S. Provisional Application No. 60/642,964 filed on Jan. 11, 2005 and the disclosure is incorporated herein by reference.

This invention relates to a series of chemical formulations for the decontamination and destruction of hazardous and toxic chemicals.

FIELD OF THE INVENTION

BACKGROUND OF THE INVENTION

Since World War I, decontaminants and methods for their use have been sought that are effective in the neutralization and destruction of chemical toxants, which include chemical warfare agents (CWAs) and Toxic Industrial Chemicals (TICs). Such chemicals often have properties that make their destruction challenging. One is the propensity toward reactions that lead to persistent and toxic reaction products. Another is insolubility in aqueous solutions. Yet another is the propensity toward reactions that form 'protective' reaction products that limit mass transfer and contact between a decontaminant and the toxant. Also, high viscosity makes mixing with and solubilization by a decontaminant slow. Further, such toxants often have several reactive sites on each molecule, so that stoichiometric demands require many moles of decontaminant active ingredients for reaction with each mole of toxant.

As a result of these characteristics, which make decontamination difficult, decontamination has generally meant removal instead of neutralization or destruction. Some common decontaminants, such as chlorite bleach, are known to lead to reaction by-products that are nearly as toxic as the original agent, but are also more persistent, i.e., resistive to degradation by 'weathering'. Generally, destruction of toxants is most favorable in the alkali pH regime. However, the use of high pH decontaminants, which typically have pH higher than 10, result in corrosion and degradation of surfaces that are treated with the decontaminant.

The insolubility and viscosity characteristics of toxants often makes it necessary to use decontaminants containing surfactants and solvents and to mechanically mix the decontaminant with the toxant. Thus, mops, brooms, brushes, scrapers, and high pressure sprayers are generally associated with decontamination operations. A consequence of such methods for decontamination is the generation of a waste material stream that typically contains hazardous materials. The use of high pressure washers, which effects toxant removal and also local mixing of decontaminant and toxant, leads to aerosolization of toxant and produces a toxic plume and the potential for recontamination.

There are several issues associated with the decontamination of CWA and TIC contaminated objects. These are:
(1) the degree of neutralization versus removal of the toxant,
(2) the corrosivity of the decontaminant and the environmental regret associated with its use,
(3) the logistical requirements for effective decontamination operations, e.g., the quantity of decontaminant that is necessary to treat a challenge quantity of toxant,
(4) operational practicality, e.g., the avoidance of mechanical mixing, mopping, brushing, scraping, and wiping, and the 'pot life' of the decontaminant, once it is prepared for use,
(5) the shelf life of the decontaminant, and
(6) the cost of the decontaminant.

Present methods and decontaminants for toxants, in particular CWAs and TICs, have undesirable attributes in respect to one or more of the issues listed above. Most common is corrosiveness and environmental regret, which result in unacceptable damage to objects that have been decontaminated, and the necessity of mixing, mopping, brushing, scraping, and wiping, which makes decontamination operations labor intensive and time consuming.

SUMMARY OF THE INVENTION

The present invention is a decontaminant formulation, which comprises a composition that is prepared within a few hours prior to use and made from the mixture of two or more parts. In one part is a peroxide, which is stabilized for long shelf life; and an organic co-solvent. In another part is a combination of an amine, which in reaction with the peroxide of the other part is a source of perhydrolysis species; phase transfer catalyst, which may be one or more quaternary ammonium compounds; metal oxide catalyst, which in reaction with the peroxide of the other part produces the oxidant 'M' Ox$_{+n}$; chemical base, which is a source of HO$^-$; and pH buffering compounds. The balance of the composition is water, preferably de-ionized water that has a low trace metals content.

The present invention is a decontaminant that is able to neutralize a broad spectrum of contaminants and toxants and having improved reactivity and toxant solubilization, especially for organophosphorus agents, for sulfur mustard (HD), and for other difficult to decontaminate chemicals.

The present invention may decontaminate chemical agents and TICs and may be applied by a variety of means, which include electrostatic spraying as an aerosol onto a contaminated object, material, or surface, and may rapidly neutralize toxants, including depositions of such toxants at high challenge levels, and to accomplish the treatment with excellent stoichiometric efficiency. It is anticipated that such a decontaminant will be useful to emergency responders, or anyone who may respond to mitigate chemical contamination. In one aspect the invention is a decontaminant composition comprising a peroxide; an organic co-solvent; an amine, which in reaction with the peroxide is a source of a perhydrolysis species; a phase transfer catalyst comprising at least one quaternary ammonium compound; a metal oxide catalyst; a chemical base; and at least one pH buffering compound.

In another aspect the invention is a shelf-stable decontaminant composition, the composition comprising a first part and a second part. The first part comprises a stabilized peroxide and an organic co-solvent. The second part comprises an amine; a phase transfer catalyst, the phase transfer catalyst comprising at least one quaternary ammonium compound; a metal oxide catalyst, the metal oxide catalyst in reaction with the peroxide of the other part producing an oxidant 'M' Ox$_{+n}$; a chemical base, the chemical base being a source of HO$^-$; and at least one pH buffering compound.

In yet another aspect the invention is a decontaminant composition comprising 15% hydrogen peroxide; 3.99 mM phosphonate detergent; 20% propylene glycol n-propyl ether; 0.436 M N-benzylamine; 1.50% hexadecyltrimethylammonium bromide; 0.127 M tetrabutylammonium hydroxide; from 1 mM to 4 mM MoO$_4^=$; and 0.111 M sodium hydroxide.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
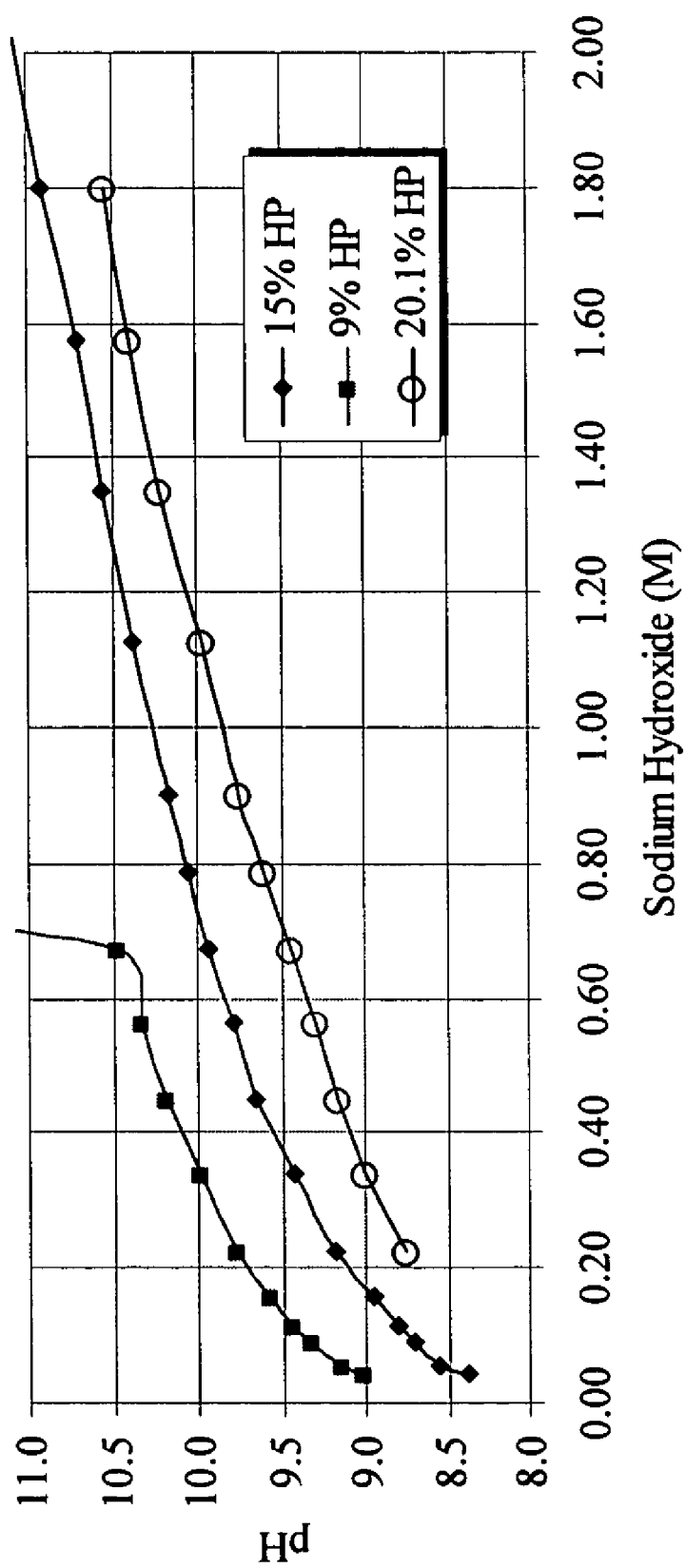
FIG. 1. The relationship between pH and NaOH and hydrogen peroxide concentrations. A range in hydroxide and peroxide concentrations for which the pH remains between 9.0 and 10.0 is shown.
Figure 2:
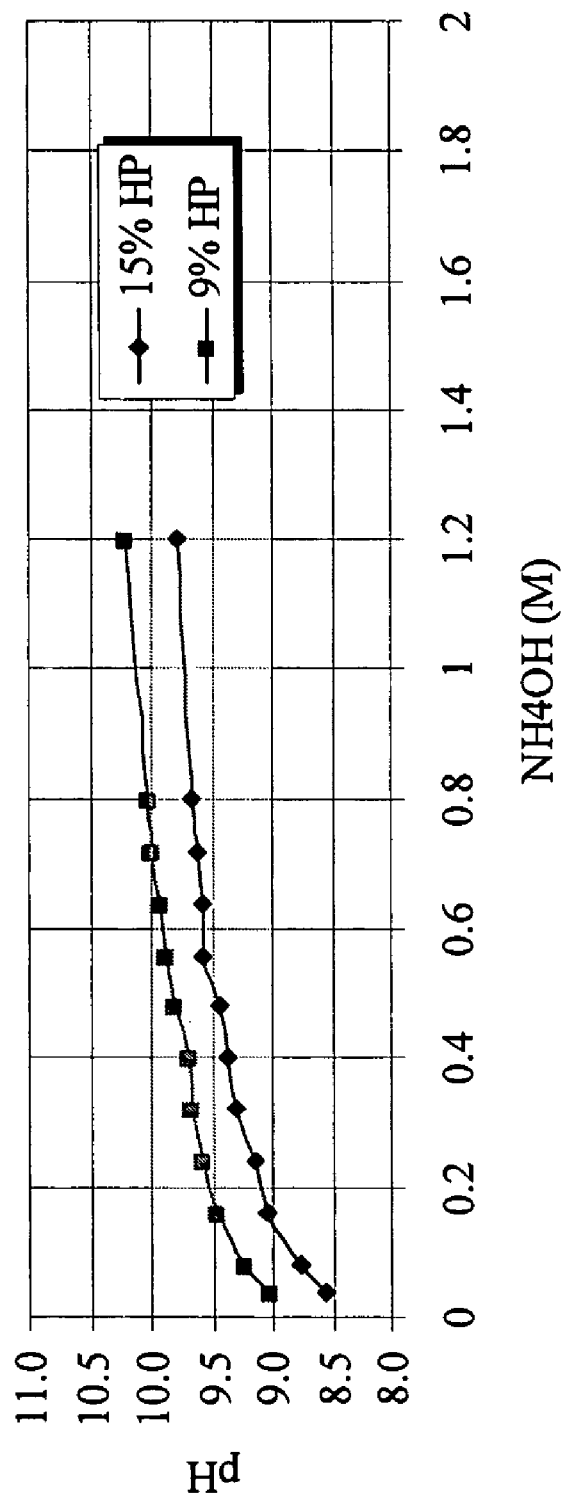
FIG. 2. The relationship between pH and $NH_4OH$ and hydrogen peroxide concentrations. A range in hydroxide and peroxide concentrations for which the pH remains between 9.0 and 10.0 is shown.

The principal active species in the formulation are the peroxy anion ($HOO^-$), which causes perhydrolysis, and the oxidant 'M'$Ox_{+n}$. The formulations contain additional potentiating ingredients which improve toxant solubility and reactivity, and which result in good surface interaction and wettability by the decontaminant. Three typical formulations are exhibited in Table I. These formulations are called 'Chemical Decontamination Solution (CDS) —X, —Y, and —Z, and vary by their content of metal oxide catalyst. In Table I, the ingredients are listed in row 2 (from the top of the sub-table for each formulation), e.g., $H_2O_2$, the starting concentrations are given in row 3, e.g., $H_2O_2$: 30%, the volume added to the mixture is given in rows 4 and 5, e.g., 2.50 ml of 30% $H_2O_2$, and the final percentage or concentration in the composition is given in the bottom two rows, e.g., $H_2O_2$: 15%.

TABLE I

Examples of formulations of the Chemical Decontamination Solution (CDS)

| CDS-X Part A | | | CDS-X, PART B | | | | | | |
|---|---|---|---|---|---|---|---|---|---|
| $H_2O_2$ | PGPE | Dequest16 | CTAB | BAM | TBAH | NaOH | $MoO_4^=$ | DIW | Total |
| 30% (mL) | (mL) | 1.33 M (mL) | 100.0% (g) | 99.00% (mL) | 55% (mL) | 33.30% (mL) | (1M) (mL) | (mL) | (mL) |
| 2.50 | 1.00 | 0.015 | 0.075 | 0.240 | 0.30 | 0.050 | 0.005 | 0.82 | 5.00 |
| 15.00% | 20.0% | 3.99 (mM) | 1.50% (%) | 0.436 (M) | 0.127 (M) | 0.111 (M) | 1.00 (mM) | | 0.674 Total Base |

| CDS-Y Part A | | | CDS-Y, PART B | | | | | | |
|---|---|---|---|---|---|---|---|---|---|
| $H_2O_2$ | PGPE | Dequest16 | CTAB | BAM | TBAH | NaOH | $MoO_4^=$ | DIW | Total |
| 30% (mL) | (mL) | 1.33 M (mL) | 100.0% (g) | 99.00% (mL) | 55% (mL) | 33.30% (mL) | (1M) (mL) | (mL) | (mL) |
| 2.50 | 1.00 | 0.015 | 0.075 | 0.240 | 0.30 | 0.050 | 0.010 | 0.81 | 5.00 |
| 15.00% | 20.0% | 3.99 (mM) | 1.50% (%) | 0.436 (M) | 0.127 (M) | 0.111 (M) | 2.00 (mM) | | 0.674 Total Base |

| CDS-Z Part A | | | CDS-Z, PART B | | | | | | |
|---|---|---|---|---|---|---|---|---|---|
| $H_2O_2$ | PGPE | Dequest16 | CTAB | BAM | TBAH | NaOH | $MoO_4^=$ | DIW | Total |
| 30% (mL) | (mL) | 1.33 M (mL) | 100.0% (g) | 99.00% (mL) | 55% (mL) | 33.30% (mL) | (1M) (mL) | (mL) | (mL) |
| 2.50 | 1.00 | 0.015 | 0.075 | 0.240 | 0.30 | 0.050 | 0.020 | 0.80 | 5.00 |
| 15.00% | 20.0% | 3.99 (mM) | 1.50% (%) | 0.436 (M) | 0.127 (M) | 0.111 (M) | 4.00 (mM) | | 0.674 Total Base |

Material sources:
1. 30% hydrogen Peroxide, Sigma.
2. PGPE = 99%, propylene glycol propyl ether, Chemisphere Corp.
3. TBAH = 40%, tetrabutylammonium hydroxide, Sigma. 55% TBAH from SACHEM, Inc.
4. NaOH = sodium hydroxide, 50% solution, Fisher Sci.
5. Dequest 2016, Solutia, Inc.
6. CTAB = 99%, cetyltrimethylammonium bromide, Alfa Aesar.
7. BAM = benzylamine, Sigma.
8. $MoO_4^=$ = potassium molybdate, Sigma.
9. DIW = deionized water The effectiveness of the peroxy anion in degrading organophosphorous compounds and CWAs has been previously reported, and mechanisms for the perhydrolysis of these compounds have been proposed, in the prior art. The parallel use of oxidant species to degrade organo-sulfides and other toxants that may resist perhydrolysis is made practical by the selection of stabilizers, buffers, catalysts, and bases in the appropriate proportions. The result is that the CDS formulations have performance that is superior to other similar decontaminants. The CDS formulations have excellent, broad spectrum DE, good material compatibility, i.e., low corrosivity, a capacity for high agent/CDS loading. Less CDS is needed to achieve high DE, which leads to a 'small logistical tail', and an extraordinary capability for agent solubilization, i.e., decontamination that requires no scrubbing.

Perhydrolysis:

The mixing of Part A with Part B produces the perhydroxide anion which will react with hazardous chemicals that have a phosphorus center, a carbon center and/or a carbon-carbon double bond to form unstable peroxide intermediates, which will undergo additional decomposition via an irreversible pathway with a very high efficiency. One perhydrolysis mechanism involves the apical attack of the perhydroxide anion on the phosphorus atom center to form the trigonal bipyramid intermediate, which undergoes a pseudorotation equilibrium shift to position the better leaving group in the apical position. In the case of the organophosphorus compounds, this often involves the positioning of the fluoride or cyano moieties and the thioethyl-(2-diisopropylamino) functionality in the apical position for overall formal displacement.

The decontamination capacity and efficiency of the CDS formulation against organophosphorus toxants is strongly dependent on the total base concentration and less dependent on the concentration of hydrogen peroxide, which is in excess and also functions as a pH buffer for the decontamination formulation. Hydrogen peroxide is a weak acid but stronger than water.

$$H_2O_2 \xrightleftharpoons{K=2.24\times10^{-12}} HOO^- + H^+$$

It is clear that perhydroxide anion concentration is strongly dependent on the pH of the solution, such that higher pH levels lead to higher perhydroxide anion concentrations. Because hydrogen peroxide is a stronger acid than water, hydrogen peroxide dissociation is more favored than water dissociation, and its concentration is higher than hydroxide anion, provided that the initial hydrogen peroxide concentration is high enough. CDS is a perhydrolysis dominant decontamination reagent against organophosphorus pesticides and nerve agents. For these toxants, the decontamination capacity is dependent on the effective concentration of perhydroxide anion. For a fast and effective decontamination reagent, the effective perhydroxide anion concentration should be high enough to maintain a stoichiometric excess during the chemical reaction. In order to have an effective perhydroxide anion concentration for the decontamination reagent (pH range of 9 to 10), one option is to use a high concentration of hydrogen peroxide, and another option is to select a suitable strength base. In the latter option, the base capacity should be large in comparison with a strong base, so that the suitable strength base and hydrogen peroxide will form a buffer system to maintain the pH in the desired range and also achieve effective decontamination of organophosphorus toxants with the developed formulation. For example with a fixed concentration of hydrogen peroxide, such as 15%, to maintain the pH between 9 and 10, the base concentration should be in a range of 0.25 M to 0.70 M when sodium hydroxide is employed as a base (FIG. 1). This concentration range is greater than 1 M when ammonium hydroxide is employed as the base (FIG. 2) to maintain this base capacity during the course of the reaction.

Catalytic Oxidation:

The reaction is to effectively oxidize low valence sulfur or nitrogen involved in CWAs and TICs. The following reactions are illustrative of the sulfur mustard (HD) oxidation mechanism.

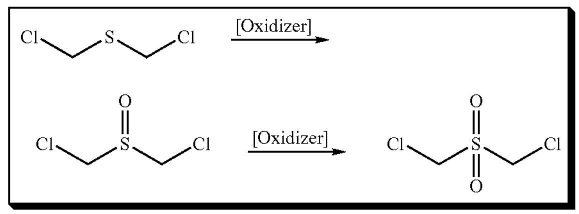

Although the oxidation reaction rate may be slower than the perhydrolysis reaction rate, the oxidation capacity of CDS can be much higher than for perhydrolysis.

The CDS may be mixed within a few hours, typically 4 hours, prior to use by combining all of the ingredients and mixing them. For long shelf life, a preferred embodiment is to make the CDS within a few hours, e.g., within 2 hours at ambient temperature of 30° C., and no more than 24 hours at ambient temperature of 0° C., prior to use as a mixture of two parts. These two parts are described as follows.

Formulation of the First Part, Part A

In the formulation, the preferred peroxide is hydrogen peroxide, which is the source of perhydroxyl anion and catalytic oxidant. The peroxide is also a critical part of the pH buffering system. It is commonly available in low cost technical grades as aqueous solution with concentration up to 70%. For a preferred embodiment, a concentrate containing 20 to 35% hydrogen peroxide is amenable to good stability, packaging, and handling. In such a preferred embodiment, the peroxide concentration may be selected so that the mixing of Part A and Part B will result in the desired hydrogen peroxide concentration in the CDS, which in the preferred range is 8 to 20% peroxide. A concentration of 15% hydrogen peroxide in the combined Parts A and B is found to have very high decontamination effectiveness for a toxant/CDS loading ratio of 30 mg/ml for most toxants and a ratio greater than 50 mg/ml for some organophosphorus compounds.

To aid in dissolving the toxant and low aqueous solubility materials that may otherwise limit contact between the decontaminant and toxant, such as oils and greases, a common organic solvent is necessary. Alcohols and ethers are candidate choices. However, a less polar solvent is preferred for a broad spectrum decontaminant, i.e., one that is effective for many types of toxants. The organic solvent may be considered to be a co-solvent. One such preferred solubilizing solvent is propylene glycol n-propyl ether (PGPE). In a preferred embodiment, PGPE in the combined mixture of Parts A and B is in a concentration of 10 to 30% by weight.

Stabilization of the peroxide concentrate is accomplished by a phosphonate detergent/sequestering agent. An example is Dequest™ 2010/2016, which is manufactured by Solutia, Inc. These detergents stabilize the hydrogen peroxide for an improved shelf life of Part A. Such stabilizers may be used in a range of 0.1 to 20 mM, with a preferred embodiment being in the range of 2 to 5 mM.

Formulation of the Second Part, Part B

In the second part of the formulation, Part B, are mass transfer catalyst, amine, selected bases, metal oxide catalyst, and a balance of water. A preferred mass transfer catalyst is the quaternary ammonium compound, hexadecyltrimethylammonium bromide (CTAB). The weak organic amine acts with the peroxide as a buffer system to maintain the pH so that it is less than 9.5 for the formulations shown in Table I. The combination of catalytic oxidation attack and perhydrolysis makes for effective degradation of the toxant, while the maintenance of the pH at moderate alkaline values makes for low corrosivity and good material compatibility properties. In a preferred embodiment, the weak base amine is a primary aliphatic amine, a preferred example being benzylamine (BAM). BAM, which is a weak base, and tetrabutylammonium hydroxide (TBAH) and sodium peroxide react with hydrogen peroxide to provide the anions for the perhydrolysis. Longer aliphatic chain ammonium hydroxides are also suitable. A strong base, such as sodium hydroxide (NaOH), provides a source of $HO^-$, but other soluble bases may be used.

The metal oxide catalyst may be any having a metal or a combination of metals in the family of molybdenum on the periodic table of elements. However, for low cost, high effectiveness, and availability, a molybdate catalyst is preferred. A tungstate catalyst is also an effective choice. The concentration of the metal oxide catalyst may be in a range of 0.1 to 10 mM in the combined mixture comprising CDS. In preferred embodiments, the catalyst is $MoO_4^=$ and is in the concentration range of 0.5 to 5 mM in the combined CDS mixture.

There are ranges of concentration in the combined mixture comprising CDS for the ingredients of Part B or corresponding multiple parts, for which the CDS is found to have good DE. In preferred embodiments, the surfactant CTAB is in a concentration range of 0.25% to 7% in the combined CDS mixture, 1.00% to 2.0% being especially preferred. One base component and phase transfer catalyst may be TBAH in a concentration range of 0.01 M to 0.45 M, with 0.1 M to 0.15 M being a concentration range in a preferred embodiment of the combined mixture comprising CDS. Another base component may be an alkali metal hydroxide, such as potassium or sodium hydroxide, selected for solubility and in a concentration range of 0.05 to 0.45 M in the combined mixture comprising CDS. In a preferred embodiment, the base is sodium hydroxide in a concentration range of 0.09 M to 0.15 M. The aliphatic amine, e.g., N-benzylamine, may be in a range of 0.05 M to 1.0 M, and in a preferred embodiment is in the concentration range of 0.25 M to 0.80 M in the combined mixture comprising CDS.

It is understood that the formulations tabulated in Table I have shown good decontamination effectiveness for toxant/CDS loading ratio of 30 mg/ml. The same formulations at one half of the concentration of ingredients except will also have very good decontamination effectiveness for toxant/CDS loading ratio of approximately 15 mg/ml. Thus, the strength of the CDS may be varied according to the toxant challenge level to be decontaminated. Of course, at a greater toxant/CDS loading ratio, more CDS is needed to decontaminate a given toxant challenge level. At a toxant/CDS loading ratio as high as 171 mg/ml, for sulfur mustard (HD), CDS achieves D>50 % destruction of agent in droplets on test panels without any scrubbing, wiping, brushing, or scraping.

Dissemination of the CDS decontaminant may be made by a variety of means. The CDS can be applied to contaminated surfaces by known methods such as spraying, pouring, or by spreading with the use of an applicator such as a brush, mop, wipe, sponge, or similar means. Although actions to mix agent and CDS, such as brushing, wiping, scrubbing, scraping, etc., may result in better agent-decontaminant contract and mass transfer of reactants for thorough reactions, CDS has great ability to solubilize, i.e., dissolve, heavy deposits of agent on a surface within a few minutes without any such mixing. This is especially important in the presence of dirt, grime, oil, grease, or other surface soil. Spraying, and in particular electrostatic spraying, provides application with efficient use of the material. For a challenge comprising a gram of toxant per square meter, an application of approximately 30 ml per square meter is very effective in accordance with the loading ratio described above. This may be applied in a single spray coat. For greater challenge levels or for relatively thick deposits of contamination, repeated sprays may be made to achieve the desired loading ratio. Repeated sprays may also be used in those situations where the CDS evaporates prior to achieving the level of decontamination that is desired. The CDS is also effectively used as a decontaminating bath for objects that can be immersed in the solution. It can further be dispersed as an aerosol, especially a charged aerosol, for interaction with and decontamination of an aerosol cloud of toxant.

CDS has excellent compatibility with most materials and leads to no significant degradation of objects to be decontaminated. When used to decontaminate sensitive materials, which include highly mechanically stressed plastics and some reactive pure metals, e.g., magnesium, zinc, and aluminum, the effects of reaction between CDS and the material can be minimized by post decontamination washing or neutralization. Generally, CDS is compatible with alloys with composition including these reactive metals. For some electrical components or assemblies with conductivity properties that may be affected by wetting with CDS, e.g., high voltage insulators, post decontamination washing, neutralization, or drying may be necessary.

Testing

Testing has been performed that has demonstrated the improvements and desired characteristics of the decontaminant composition of the present invention. The superior solubilization capacity has been shown in testing with simulants, which are known to be more challenging than the corresponding agent. Decontamination effectiveness (DE) test results are described. Reaction kinetics have been determined, and the efficacy of CDS is compared to that of other decontaminants.

The extensive testing program comprised five principal elements: (1) Test methods and assay techniques were developed so that DE based on agent destruction/neutralization (in contrast to removal) could be credibly demonstrated. (2) Simulants were selected for their close relation to agent-decon chemistry, and robust agent-simulant correlations were established. (3) Thorough testing with simulants has been conducted against a variety of realistic challenge deposition levels. (4) Extensive testing has been conducted with chemical warfare agents. (5) Comparative testing against other decontamination technologies has been performed.

Scalability for process and testing has also been addressed. This includes the important elements of the decontamination process and the corresponding elements of the sampling and diagnostic measurement process. The testing includes a range of test article sizes from vial tests on the laboratory benchtop to 10 cm×10cm (100 cm²) panels. An important part of the test program is the development of improved methods and procedures, which are appropriate for testing the CDS formulations. This includes using several formats for agent deposition; for example, uniform, small dot arrays, and heavy streaks. Tests include a variety of chemical challenges on a variety of materials (e.g., glass, butyl rubber, and aluminum). Results are reported for DE tests of chem-decon with the CDS against a variety of simulants and chemical warfare agents (CWAs). The test examples have been selected for extrapolation to anticipated actual decontamination operations with good fidelity.

Materials & Methods

Chemical Simulants

Choices for test chemicals (Table II) were made based on the fidelity of the test chemical-decontaminant reaction chemistry and decontamination interactions. The selections were chosen so the potential leaving group or reactive center has a functionality that is representative of chemical warfare agents and so that similar fimctionalized products are formed. The test chemicals that are not chemical warfare agents, but have good fidelity in decontaminant testing, are referred to herein as simulants. Similarity of water/organic solvent solubility properties of the simulants to the agent are also important because of its effect on decontamination solution-agent mixing and dispersion characteristics. Physical similarities, such as vapor pressure and viscosity are considered secondary, but critical, attributes; as such properties also affect the decontaminant-agent interaction.

TABLE II

Chemical Simulant and Agents Employed in the Study

| AGENT | SIMULANT |
|---|---|
| Methylphosphonofluoridic Acid, (1-methylethyl) Ester (GB, Sarin) | Diisopropyl fluorophosphates (DIFP) |
| Methylphosphonothioic Acid, S-[2-[bis(1-methylethyl)amino] ethyl] O-ethyl Ester, (VX) | Malathion |
| 2,2'-Dichlorodiethyl sulfide, (HD) | Di-propyl sulfide (DPS) Di-n-butyl sulfide (n-BS) 2-Chloroethyl ethyl sulfide (CEES) 2-Chloroethyl phenyl sulfide (CEPS) |

Prior art uses indicate the decontamination reaction chemistry between a G-series agent (in particular, GB) forms the phosphonic acid form of molecule—that is, the fluorine is replaced by a hydroxide. One of the byproducts is $F^-$. Because of the possible effects $F^-$ could have on the decontamination formulation, a high priority was placed on selecting a simulant with this pathway. An obvious choice for the simulant was DIFP (FIG. 1), a material having the same kind of cholinesterase inhibition activity as the G-agents, which supports its likelihood of having the same reaction chemistry as a G-agent.

Malathion was chosen as the VX simulant because it possesses the desired P—O and P—S bonding arrangement that will distinguish between the phosphorus-sulfur and phosphorous-oxygen bond cleavage. The former is the desirable route for degradation of VX, whereas the latter has the potential to form the toxic byproduct EA2192. The physical properties of Malathion are also similar to those of VX. One of the testing issues with Malathion is that it has several potential reactive sites compared to VX. Malathion, as an organodithiophosphate, has two phosphorus-sulfur (P—S) bonds in addition to two phosphorus-oxygen (P—O) bonds. With phosphorus' known propensity for oxygen, the conversion of the phosphorus-sulfur dative bond to a phosphorus-oxygen dative bond is a very competitive reaction, which in the case of Malathion produces the known phosphorothioate metabolite malaoxon. This is a known degradative pathway for other decontamination technologies with Malathion. Competitive hydrolysis of the two carboxylate ester centers with the phosphorodithioate ester center is also another degradative pathway. Therefore, it is expected that the stoichiometric ratio between decontaminant to Malathion will be greater than the ratio between decontaminant and VX.

Four chemicals were identified as simulants for sulfur mustard (HD) because they offer similar decontamination chemistry: DPS, n-BS, CEES, and CEPS. It has been proposed that the first step in HD hydrolysis is an intramolecular hydrolysis with sulfur displacement of the chloride from the β-carbon, forming an intermediate cyclic sulfonium salt, which then is susceptible to nucleophilic attack by water or other nucleophiles with ring opening of the sulfonium ion. The products of this reaction are the hemi-mustard and hydrogen chloride. The hemi-mustard continues the same process with the other chloride of HD, eventually forming the thiodiglycol product as well as several additional aggregates. CEES (half-mustard) was chosen as a simulant because it possess the two finctionalities, chloride and bis-substituted sulfur, comparable to HD.

Many researchers in the field have suggested that the primary reaction path for oxidative decontamination of HD was at the central sulfur atom and not the chloride. Like HD, DPS and n-BS possess a sulfur atom which is expected to be converted to a sulfoxide or sulfone upon oxidation. Reactions of this type, for example the oxidation of a dialkyl sulfide to the sulfoxide or sulfone, are well documented in the prior art. Early in our studies, we observed that the reactivity of DPS and n-BS in our decon reagent did not correlate well with the reactivity between HD and our decon reagent. We then began to employ CEPS, which has chloroethyl functionality on one side of the sulfur and a phenyl group on the other arm.

According to the prior art, hydrolysis of HD in the presence of water is rapid, but the reaction is severely limited by the low solubility of HD in an aqueous environment. Consequently, a certain amount of hydrolysis occurs at the HD/water interface; and upon formation of polymeric products, diffusion stops. Therefore, while CEES is a good simulant for the hydrolysis mechanism, it is not a good simulant for HD decon because it does not reflect the insolubility issues with HD. DPS and n-BS lack the chloride and therefore react at the sulfur atom, but they are easy to decon because they do not simulate the redox potential and solubility of HD. Of the four simulants used in this study, CEPS provides the best combination of low solubility and chemical reactivity. Our experiments indicate that hydrolysis and subsequent polymerization are not a part of the CEPS degradation pathway, and the sulfur is the only potential reactive site for oxidation reaction.

Instrument Calibration

Calibration curves for the specific analytes are prepared prior to analysis of the actual test material in all analyses. Also, as part of the standard analytical procedure, the method detection limit (MDL) is determined for each analyte under the chromatographic conditions to be applied. For each test conducted, the MDL is considered valid for the test material only if the signal to noise (S/N)>3/1. Calibration curves are generated routinely for each test material, and quantitation is obtained by an internal standard method. The calibration curve is the ratio of the analyte peak area and the internal standard peak area plotted versus the known concentration of each analyte. For phosphorus-only containing materials, the analyte calibration curves are plotted using a linear regression least fit through the origin. For the sulfur containing materials, the analyte calibration curves are plotted using a quadratic fit forced through the origin.

Controls

The tests are conducted rigorously as 'controlled experiments'. For each vial test, a 100% 'Recovery' sample is prepared by spiking the test material at the test level into the chromatographic carrier solvent. In addition, each test has a 'Blank' sample and a 'Positive Control' sample. The 'Blank' sample contains only the CDS, minus the oxidative components and contains no test simulant. The 'Blank' sample is subjected to all of the same manipulations as the actual test. Analysis of the 'Blank' sample demonstrates whether any interference develops from the CDS, minus the oxidants, or the extraction/chromatographic solvent. The 'Positive Control' sample is spiked with the CDS minus the oxidants and also with the test material. The 'Positive Control' sample is subjected to the complete procedure with treatment, extraction, and analysis. This permits the determination of chromatographic interferants with the test material.

Key Parameters and Technical Approach to Testing

The key parameters are defined and measured, and the test procedure is outlined in the following discussion. The DE is defined as the ratio of the remaining quantity of chemical challenge and the initial quantity of challenge. Typically plotted is the percentage of the challenge that is destroyed or lost from the test object, i.e., D=100 (1−DE). The assay to determine the amount of remaining challenge on the surface or in the vial comprises sampling/extraction into non-aqueous phase (typically with hexane extraction) and injection into either an high performance liquid chromatograph (HPLC) instrument or into a gas chromatograph/mass spectrometer (GC/MS) or gas chromatograph/pulsed flame photometric detector (GC/PFPD). These chromatographic instruments must be calibrated with a known 'internal' standard, and both the retention time and integrated areas under analyte peaks must be checked for consistency during the tests. With the HPLC, the MDL corresponds to D~99.99%, typically, i.e., DE corresponds to 4 logs reduction. In principle, GC/MS and GC/PFPD can achieve an additional order of magnitude or two, but this depends on background and interference by other compounds. An MDL is usually taken as a signal to noise ratio of at least 3. At the end of the specified test interval, the sample is extracted into hexane prior to injection into the assay instrument.

The fundamental steps in the DE tests comprise the following: The pre-test steps include the assay of the challenge material, instrument calibrations, and test object preparation. The challenge is applied to the test object and to a 'positive' control set. There is also a 'blank' control in the DE tests. The test objects are treated. After treatment, samples are taken, and the decon action is stopped by extraction into a non-aqueous solvent. The remaining agent is then analyzed.

Chemical 'Vial' Tests

Vial tests of chemical decontamination are performed to determine stoichiometric requirements for several-log destruction of chemical agents and to study reaction kinetics.

'Capped vial' tests are performed to determine the percentage of agent lost or destroyed, D. In the test procedures, which were developed at Clean Earth Technologies, LLC (CET), a few microliters (μl) of challenge are introduced into a vial containing 0.2 ml (200 μl) of decontaminant. Typically, the ratio of challenge to decontaminant is 30 mg/ml. For a 10 g/m$^2$ challenge, this corresponds to a decon solution application rate of 330 ml/m$^2$. Each experiment is conducted in triplicate. The initial mixed solution is shaken by hand for a few seconds and is then allowed to stand at ambient temperature for a total of 20 minutes. The mixture is then extracted with 2-4 mls of reagent grade hexane and subjected to instrumental analysis without concentration. Instrumental analyses are conducted with either a capillary gas chromatograph interfaced with a mass spectrometer (GC/MS), a high performance liquid chromatograph (HPLC) interfaced with a mass spectrometer (LC/MS), or an HPLC with ultraviolet (UV) or fluorescence detection. The GC/MS instrument permits the monitoring of the simulant parent ion for specific identification as well as quantitation against an internal standard.

After test techniques were developed and refined at CET, the procedures were transferred to MRI and incorporated into their standard operating procedures (SOPs). Modifications introduced at MRI included the addition of the test simulant to 0.3 ml (300 μl) or more of CDS, with the appropriate scaling of the test simulant to maintain the same reactant ratios as CET used. As in CET's Standard Operating Procedure (SOP), each experiment was conducted in triplicate. The volume of hexane extractant was also scaled accordingly. Analyses of the hexane phases were conducted at MRI utilizing a dual column capillary GC equipped with pulsed flame photometric detector (PFPD) and LC/MS for EA2192 analysis.

Chemical Panel Testing

Figure 6:
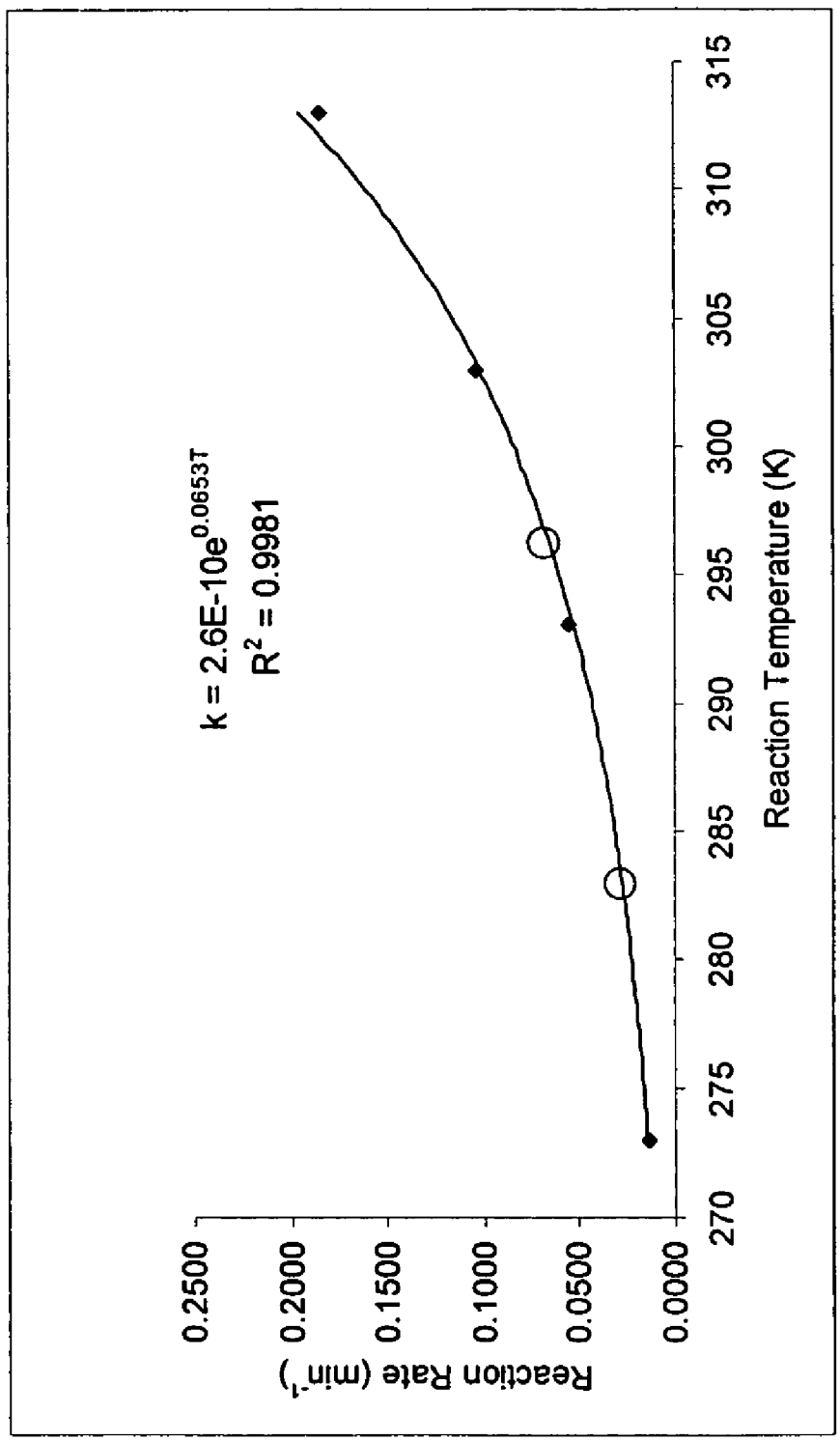
FIG. 6 Effect of Temperature on CDS Reaction Rate.

The efficacy tests span a range of test scale size and agent or simulant challenge deposition (e.g., an array of drops and line streaks, see FIGS. 4 and 6). Panel tests with various coupon materials are performed with challenge as an array of pipetted droplets (nominally~2 μl each) with a spatial average deposition ~5-10 g/m$^2$ challenge level. Such a deposition corresponds to the droplets that can precipitate from an aerosol cloud. Severe challenge deposition tests are also performed on panels on which the simulant or agent is deposited as a streak of variable size. Although the spatial average is comparable to 10 g/m$^2$ in these tests, the locally heavy deposition corresponds to a 'worst case' deposition, which may correspond to deposition near a point of release of the toxant.

Panels with dimensions of 10 cm×10 cm (100 cm$^2$) were prepared. Each test was conducted in triplicate with the application of the test simulant via an 8-channel pipette delivering ~1.7 μl per pipette tip to the panel surface of a standard solution of the simulant. Each application was repeated six (6) times per panel. This type of deposition typically results in ~40% more liquid being delivered because the pipetting error is multiplied by 48. The result is that the local challenge is well over 10 g/m$^2$. The test panels were each treated with three replications of 11 pumps each of the CDS via a calibrated liquid atomizer for a total volume delivery of 4.9 ml. The panels were then placed in a plastic container with a sealable cover. After a 30-minute exposure period, 100 ml of reagent grade hexane was placed in the container and the sealed container agitated. Aliquots of the hexane are then removed and subjected to analysis to determine D for each simulant or agent.

Results of Vial Tests

The results of the shaken vial tests show that CDS has excellent DE. The results are summarized in Table III, in which the percentage of agent challenge that is destroyed ("D(%)") is shown for the agents HD, VX, and GB. Data were obtained by Midwest Research Institute (MRI).

TABLE III

Summary of CDS Effectiveness against CWAs

| CHEMICAL AGENT | FORMAT | D (%) |
|---|---|---|
| HD | Vial | >99.9997 |
| VX | Vial | >99.9997 |
| GB | Vial | >99.9996 |

Contact time = 20 min (vial)
Ratio of agent to CDS = 30 mg/ml

Figure 3:
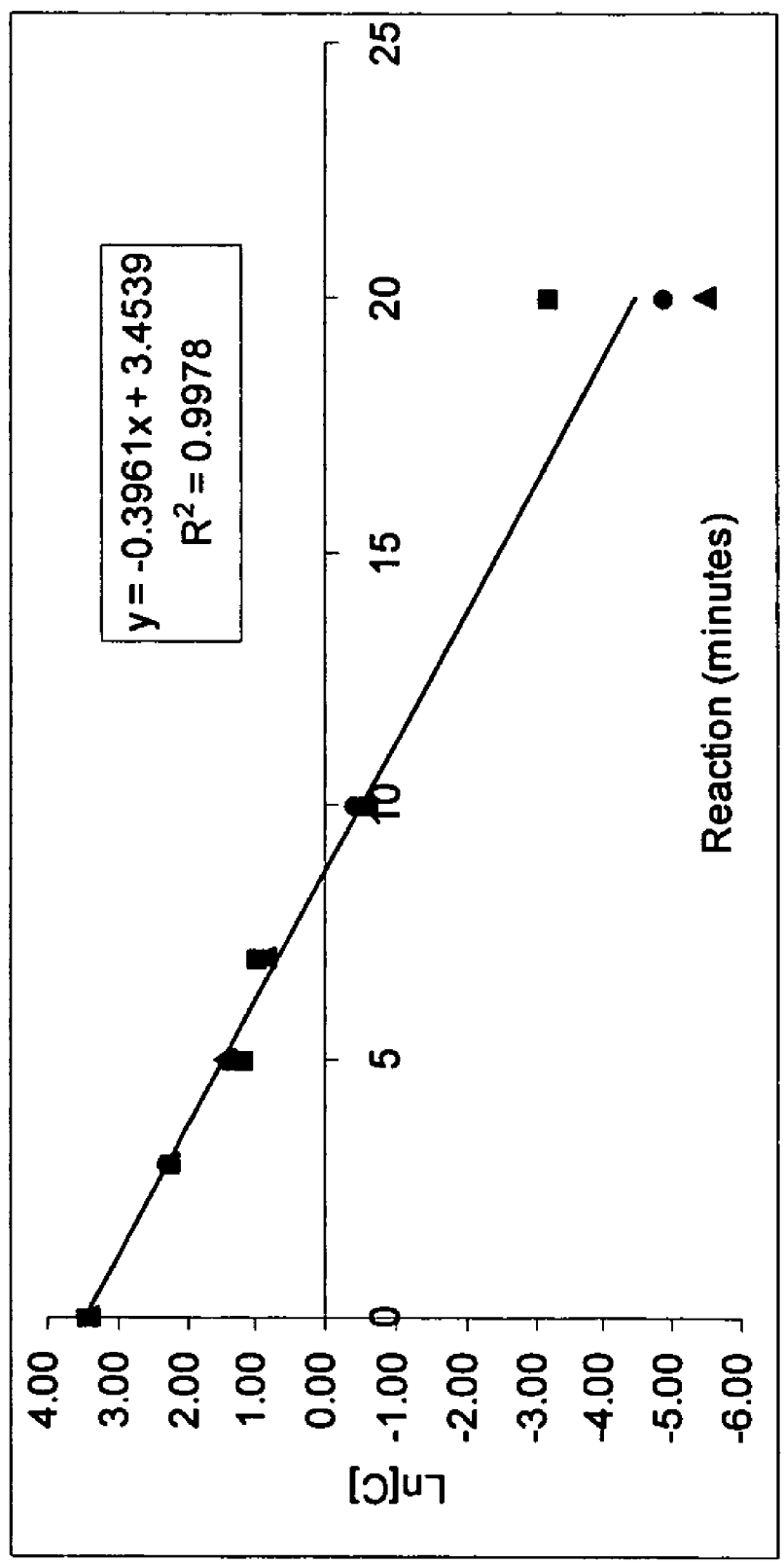
FIG. 3. Reaction Kinetics of CDS in treatment of sulfur mustard. The data appears to fit a line corresponding to a first order reaction. The data were acquired at the Midwest Research Institute (MRI). The squares, dots, and triangles represent triplicate samples of CDS degradation of HD at each time point.

In a 20-minute reaction, no HD was detected after treatment with CDS, D >99.9997% HD. The results are shown in Table IV, where ND means 'not detectable'. It can be seen that the new formulation provides outstanding DE on HD. It is also seen from confirmatory reaction kinetic studies (performed by MRI) that the reaction of CDS with HD is of first order. These data are shown in FIG. 3.

TABLE IV

Results for destruction of HD by CDS

| CDS SAMPLE | AMOUNT SPIKED (mg) | AMOUNT FOUND (mg) | PERCENT RECOVERY | D | AVERAGE D | AVERAGE AMOUNT FOUND (mg) |
|---|---|---|---|---|---|---|
| Sample 1 | 195 | ND (0.0006) | NA | >99.9997% | >99.9997% | ND (0.0006) |
| Sample 2 | 195 | ND (0.0006) | NA | >99.9997% | | |
| Sample 3 | 195 | ND (0.0006) | NA | >99.9997% | | |

Note:
Reaction volume was 200 mg of HD in 6.7 ml of CDS.
Reaction time was 20 min.
Analysis was performed using GC/PFPD.
Testing was performed by MRI.

Test results (Table V) indicate that >99.9997% of VX was destroyed within 5 minutes in CDS with a challenge level of 30 mg/ml. In comparison, results have been reported by the manufacturer of a commonly used "foam liquid" peroxide-containing composition, for which only 99.80% of VX was destroyed with its Foam liquid product in 15 minutes; the challenge level in this case was not reported.

TABLE V

Vial Test Results for destruction of VX by CDS, 200 mg Scale (MRI)

| | D (%) | Average D (%) | RSD (%) |
|---|---|---|---|
| 5-Minute Reaction | | | |
| Sample 1 | 99.9997% | >99.9997% | 0.24% |
| Sample 2 | 99.9997% | | |
| Sample 3 | 99.9997% | | |
| 20-Minute Reaction | | | |
| Sample 1 | ≧99.9999% | >99.9997% | 0.11% |
| Sample 2 | 99.9997% | | |
| Sample 3 | 99.9997% | | |

Test results indicated that >99.9996% of GB was destroyed within 5 minutes in the CDS with a challenge level of 30 mg/ml. Data are shown in Table VI. In comparison, results have been reported by the manufacturer of a commonly used "foam liquid" peroxide-containing composition, for which only 99.97% of GB was destroyed in 15 minutes with its Foam liquid product; the challenge level in this case was not reported.

TABLE VI

Vial Test Results for destruction of GB by CDS, 200 mg Scale (MRI)

| | D (%) | Average D (%) |
|---|---|---|
| 5-Minute Reaction | | |
| Sample 1 | 99.99964 | >99.9996 |
| Sample 2 | 99.99964 | |
| Sample 3 | 99.99964 | |
| 20-Minute Reaction | | |
| Sample 1 | 99.99965 | >99.9996 |
| Sample 2 | 99.99963 | |
| Sample 3 | 99.99964 | |

Kinetics of HD Destruction by CDS

It is important to establish the reaction order for HD destruction by CDS. If the reaction is not first order, then the rate of degradation decreases over time and decontamination will not go to completion within a reasonable amount of time. The result is shown in FIG. 3, and demonstrates an excellent linear relationship for first order reaction kinetics.

Results of Panel Tests

The results of the panel tests show that CDS has excellent DE. The results are summarized in Table VII in which the percentage of agent challenge that is destroyed D(%) is shown for the agents HD, VX, and GB. Data were obtained by MRI.

TABLE VII

Summary of CDS Effectiveness against CWAs

| CHEMICAL AGENT | FORMAT | D (%) |
|---|---|---|
| HD | Aluminum Panel | 99.983 |
| VX | Aluminum Panel | 99.560 |
| GB | Aluminum Panel | 99.68 |

Challenge = 5-10 g/m$^2$ (average deposition)
panel size = 100 cm$^2$
Contact time = 25 min (panel)
Ratio of agent to CDS = 30 mg/ml Comparison of DE of CDS to a Foam Decontaminant The efficacy of CDS was compared to a commonly used "foam liquid" peroxide-containing composition. This product is applied as foam, and requires scrubbing and more than one application to achieve decontamination. In this test example, the product was mixed according to directions and used as a liquid (subsequently referred to as "the Foam liquid"). In this test, CEPS was never completely dissolved in the Foam liquid in 20 minutes, so continuous shaking took place during the 20-minute reaction. In marked contrast, CEPS was completely dissolved in CDS with minimal shaking after several seconds. The CDS formulations have excellent solubilizing ability for all tested simulants and agents, including HD, which is not soluble in most decontamination reagents. Greater than 30 mg/ml HD can be very quickly dissolved in the CDS formulations in ~2 seconds of shaking. It is also found that the CDS-Z formulation achieves greater DE than the Foam liquid in the destruction of the simulant CEPS in a shaken vial test.

The difference in performance between CDS and the Foam liquid is dramatic in the panel tests. FIG. 4 shows two methods of challenge application using Malathion (VX simulant). This simulant was chosen for its insolubility, to determine how well CDS works in a practical setting. Equal amounts of Malathion were deposited on aluminum panels (10 cm×10 cm) at the challenge level of 10 g/m$^2$ in the form of an array of 2 µl drops or one continuous streak. One technical difficulty with this test is that the measuring error is multiplied by the number of deposits, so that the panels containing an array of drops actually contain about 40% more challenge than the panels with streaks.

Figures 4A, 4B:
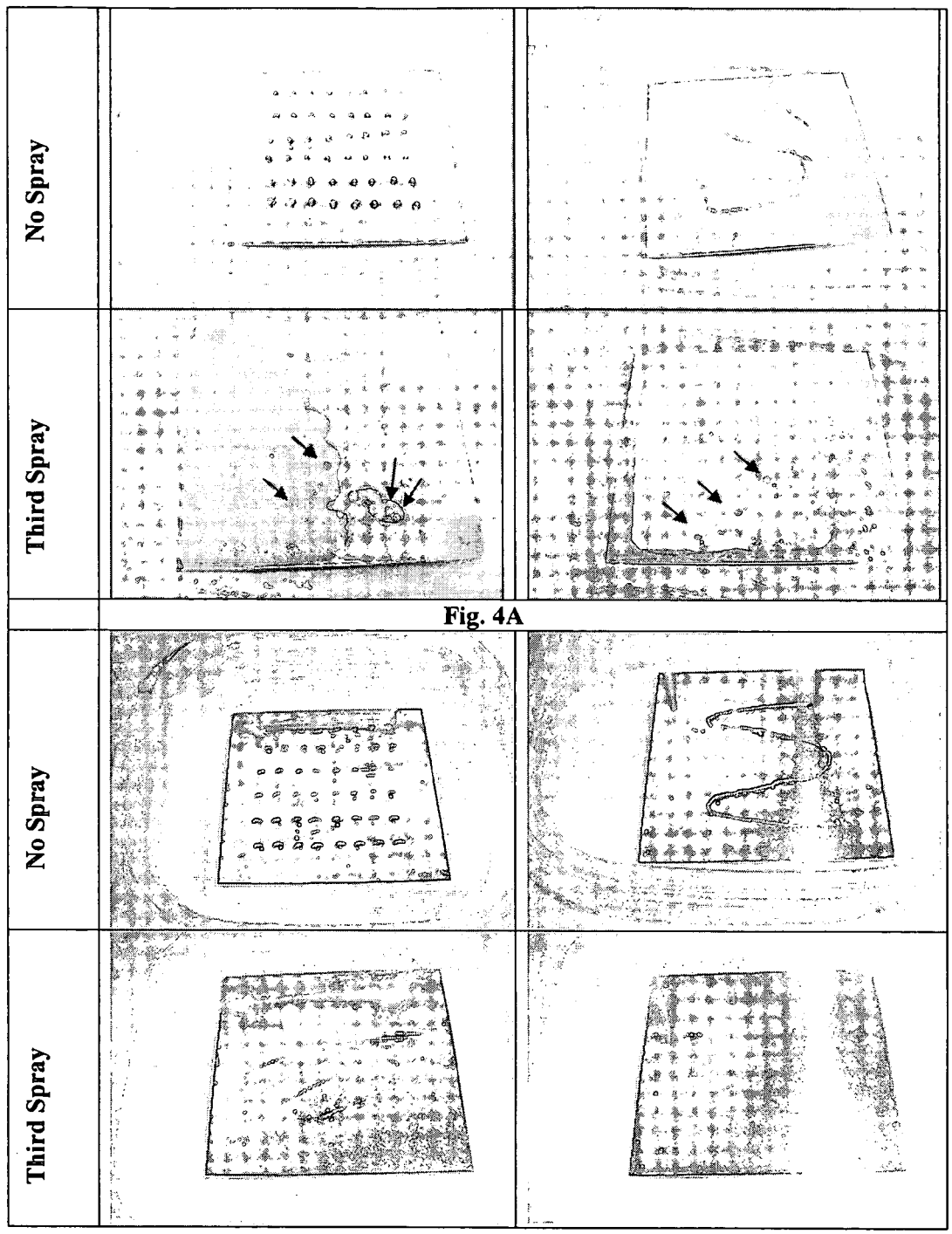
FIG. 4. Panel testing of CDS (FIG. 4B) and a commonly used "foam liquid" peroxide-containing composition (FIG. 4A) in the destruction of Malathion™. Arrows represent non-solubilized Malathion™. Comparison of the panels after spraying with decontaminant shows the superior solublization capability of the CDS.

Each panel in FIG. 4 was sprayed three times with either CDS (FIG. 4B) or the Foam liquid (FIG. 4A). A photograph was taken of the panel immediately after spraying. It can be seen on the panels sprayed with CDS that the Malathion was solubilized by the treatment without brushing (FIG. 4B). Even the heavy streak was solubilized by the third spray (FIG. 4B). In marked contrast, the Foam liquid was unable to solubilize the Malathion after three sprays and no brushing (FIG. 4A). This observation is consistent with the required operational practice of brushing the surface when using the prior art product as a 'foam' solution.

Figure 5:
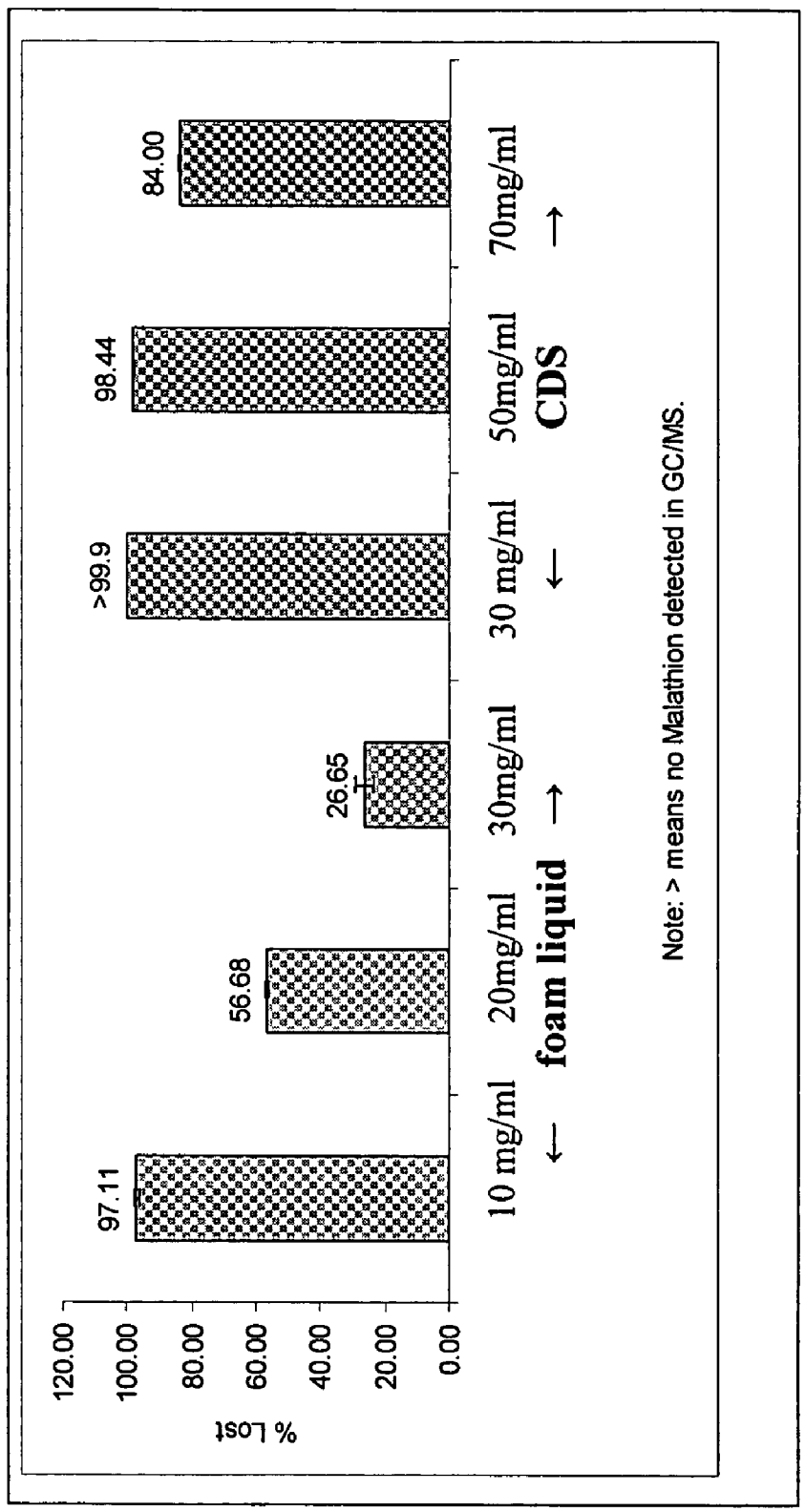
FIG. 5. Comparison of the destruction effectiveness (DE) of Malathion by CDS to a commonly used "foam liquid" peroxide-containing composition on Aluminum Panels. Panels shown in FIG. 4 were allowed to lay horizontally for 30 minutes before hexane extraction and GC-MS analysis (see Materials & Methods). Black, CDS; White, blank (no active ingredient); Hatched, "foam liquid". CDS samples were performed in triplicate and "foam liquid" was performed once.

A comparison between CDS and a commonly used "foam liquid" peroxide-containing composition in chemical decontamination has been performed using the VX simulant Malathion. In a 20-minute reaction, CDS is much more effective than the foam liquid against Malathion. As seen in FIG. 5, the foam liquid cannot completely neutralize even 10 mg/ml Malathion, while CDS neutralizes up to 50 mg/ml. In this example, the reaction was performed in shaken vials for 20 minutes as described above.

Effect of Temperature on Reaction Rate

The effect of temperature on the reaction rate was measured using the simulant CEPS because the kinetics of the reaction between CDS and this simulant had been characterized. DE of CDS against the simulant CEPS was measured at two temperatures. Knowing that the reaction is first order and the rate constant at 74° F. permits the generation of a curve (FIG. 6) which shows how temperature affects the reaction rate. It can be seen that the reaction rate increases exponentially as the temperature is increased. This means that, although the rate will slow down when temperature is decreased, it changes slowly and the reaction will still be significant as temperatures approach 32° F. (0° C., or 273 K).

It is estimated that the CDS can be used effectively in the range −10° F. (−23° C.) to 131° F. (55° C.). The freezing point of the CDS mixture is estimated to be less than −10° F. Decomposition of the hydrogen peroxide occurs above 55° C.

CDS Inactivates Ricin

A Ricin/Luciferase assay has been used to demonstrate that CDS inactivates Ricin. The assay was adapted from the rabbit reticulocyte assay developed by M. Hale of the U.S. Army Research Institute of Infectious Diseases (USAMRIID) as an assay for the inactivation of Ricin [Hale, M. L. 2001. Microtiter-Based Assay for Evaluating the Biological Activity of Ribosome-Inactivating Proteins. Pharmacology & Toxicology 88:255-260]. This assay measures the activity of the ribosome (which Ricin inhibits) and is therefore superior to antibody assays which only measure the presence of Ricin (active or inactive). The assay provides a positive signal (luminescence) when Ricin activity is absent. Therefore, the assay will produce luminescence proportional to the amount of Ricin that has been inactivated. Results show that CDS is very effective at inactivation of Ricin. We have seen a 4-log increase in counts per second (CPS) luminescence signal production (i.e., decrease in Ricin activity) following a 12-minute exposure to CDS.

Figure 7:
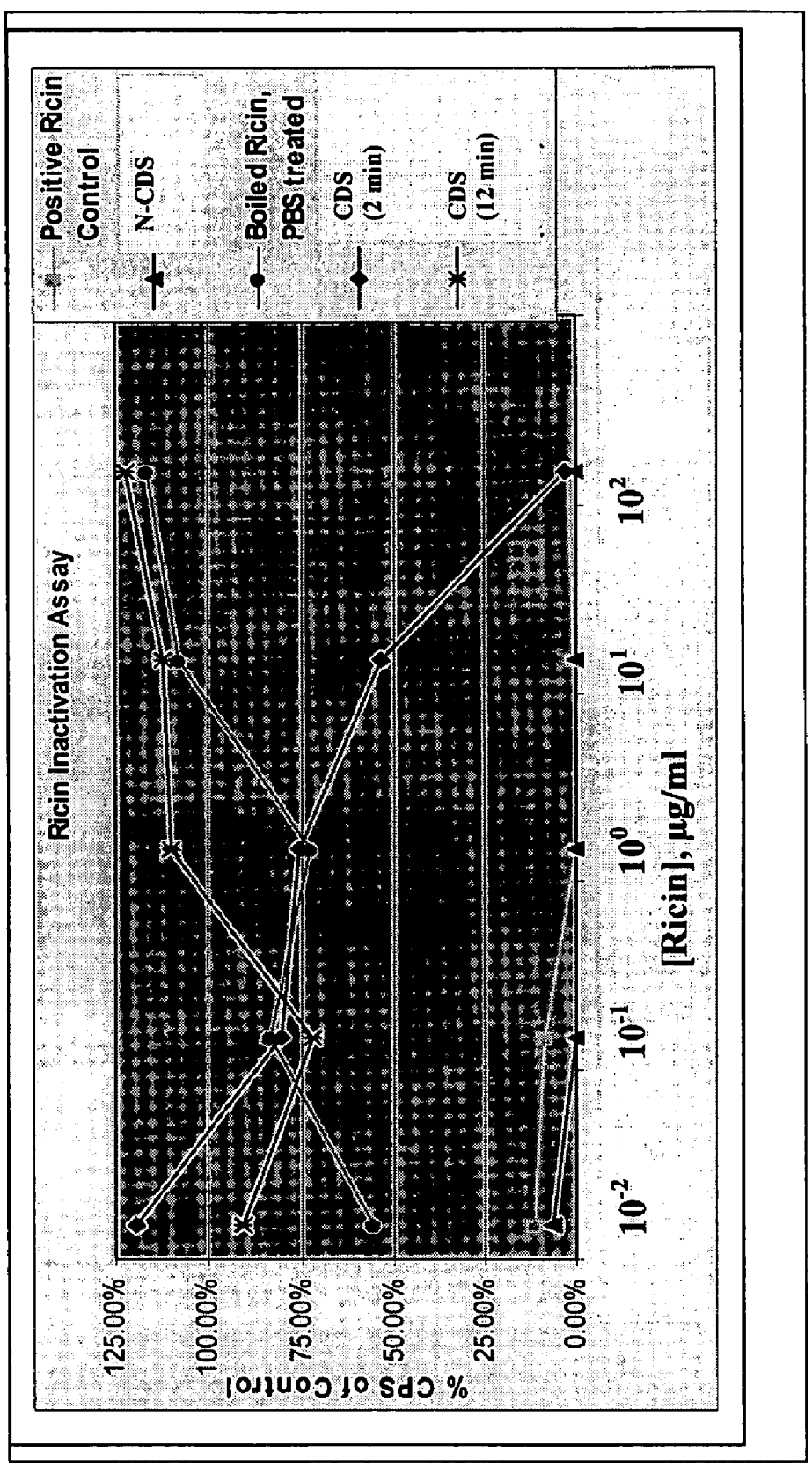
FIG. 7 Ricin Inactivation by CDS.

In this assay, Ricin that is inactivated by boiling or chemical treatment allows luminescent signal production while active Ricin prevents it. The signal produced at the highest Ricin concentration that has signal comparable to the Luciferase Translational Controls should indicate that all of the Ricin has been inactivated. FIG. 7 shows that CDS-treated Ricin dramatically decreased Ricin inhibition (i.e., inactivated the Ricin). The NATO challenge (10 g/m$^2$, and $10^7$ toxin molecules/g of material) is below the limit of detection for this assay; therefore, our challenge levels far exceed the NATO level. The highest challenge used in our testing was $4.18 \times 10^{-4}$ g of pure Ricin, which is equivalent to $3.33 \times 10^{-9}$ moles or $4.19 \times 10^{-15}$ molecules of Ricin. The lowest measurable activity in this assay is $2.25 \times 10^{-12}$ g of Ricin, which inhibited only 1.19% (average of triplicate samples) of signal produced compared to the average of the triplicate positive translation controls.

The CDS formulations have been tested and show high DE against organophosphorus and organosulfide toxants and simulants, which are representative of a broad spectrum of hazardous chemicals. The formulations show remarkable capability for agent solubilization on panels without scrubbing, brushing, or wiping.

CDS formulation advantages are a superior buffering system, which (1) provides a relatively lower pH to increase the stability of hydrogen peroxide and (2) provides a higher perhydrolysis capacity and efficiency. In addition, the CDS formulation effectively demonstrates a higher catalytic oxidation capability.

As various modifications could be made to the exemplary embodiments as described above with reference to the corresponding illustrations without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed:

1. A decontaminant composition for the decontamination of a surface or an area by destroying or neutralizing chemical toxants by perhydrolysis and catalytic oxidation, said decontaminant composition comprising:
reactive species for destroying the chemical toxants by reaction therewith;
a pH buffer system for maintaining a pH of said decontaminant composition within a predetermined range during the decontamination;
solubilization ingredients for solubilizing the chemical toxants;
a metal oxide catalyst; and
de-ionized water;
wherein said pH buffer system comprises:
hydrogen peroxide;
a phase transfer catalyst comprising at least one quaternary ammonium compound base; and
a weak base aliphatic amine; and
wherein said solubilization ingredients comprise:
an organic co-solvent,
a quaternary ammonium compound surfactant, and
said weak base aliphatic amine; and
wherein said reactive species comprise:
a perhydrolysis species formed in reaction of said hydrogen peroxide with said weak base aliphatic amine; and
a catalytic oxidative species formed in reaction of said hydrogen peroxide with said metal oxide catalyst.

2. The decontaminant composition of claim 1 wherein said quaternary ammonium compound surfactant is hexadecyltrimethylammonium bromide; said weak base aliphatic amine is N-benzylamine; said pH buffer system further contains phase transfer catalyst tetrabutylammonium hydroxide; and said pH buffer system further contains a chemical base selected from sodium hydroxide and ammonium hydroxide; and wherein said predetermined range is about 9 to about 10.

3. The decontaminant composition of claim 2 wherein said metal oxide catalyst is alkali metal molybdate or tungstate.

4. The decontaminant composition of claim 2 wherein said organic co-solvent comprises propylene glycol n-propyl ether.

5. The decontaminant composition of claim 4 comprising:
from approximately 8% to approximately 20% hydrogen peroxide;
from approximately 10% to approximately 30% propylene glycol n-propyl ether;
from approximately 0.05 M to approximately 1.0 M N-benzylamine;
from approximately 0.25% to approximately 7% hexadecyltrimethylammonium bromide;
from approximately 0.01 M to approximately 0.45 M tetrabutylammonium hydroxide;
from approximately 0.1 mM to approximately 10 mM $MoO_4^=$; and
from approximately 0.05 M to approximately 0.45 M sodium hydroxide.

6. The decontaminant composition of claim 5 comprising:
from 0.25 M to 0.80 M N-benzylamine;
from 1.00% to 2.0% hexadecyltrimethylammonium bromide;
from 0.05 M to 0.15 M tetrabutylammonium hydroxide;
from 0.5 mM to 5.0 mM $MoO_4^=$; and
from 0.09 M to 0.15 M sodium hydroxide.

7. The decontaminant composition of claim 6 comprising:
15% hydrogen peroxide;
20% propylene glycol n-propyl ether;
0.436 M N-benzylamine;
1.50% hexadecyltrimethylammonium bromide;
0.127 M tetrabutylammonium hydroxide;
from 1 mM to 4 mM $MoO_4^=$; and
0.111 M sodium hydroxide.

8. The decontaminant composition of claim 7 comprising 1 mM $MoO_4^{32}$.

9. The decontaminant composition of claim 7 comprising 2 mM $MoO_4^{32}$.

10. The decontaminant composition of claim 7 comprising 4 mM $MoO_4^{32}$.

11. The decontaminant composition of claim 2 wherein said hydrogen peroxide is stabilized by 0.1 mM to 20 mM of a phosphonate detergent.

12. The decontaminant composition of claim 2 said decontaminant composition is prepared within 2 hours prior to its use at a temperature of about 30 degrees C.

13. The decontaminant composition of claim 2 wherein said decontaminant composition is prepared within 24 hours prior to its use at a temperature of about 0 degrees C.

14. The decontaminant composition of claim 2 wherein said decontaminant composition is prepared within 6 hours prior to its use at a temperature of about 20 degrees C.

15. A method of decontaminating hazardous chemicals on a surface, comprising applying the decontaminant composition of claim 1 onto said surface.

16. The method of claim 15 further comprising applying said decontaminant composition by at least one of electrostatic spraying, pressure spraying, pouring, or spreading with an applicator.

17. The method of claim 15 further comprising leaving said decontaminant composition on said surface for at least five minutes.

18. The decontaminant composition of claim 1 further comprising a minor amount of stabilizer.

19. A shelf-stable decontaminant composition for the decontamination of a surface or an area by destroying or neutralizing chemical toxants by perhydrolysis and catalytic oxidation, said composition comprising a first part and a second part that are mixed together so that said composition resulting from the mixture has a pH in the range of about 9 to about 10 and comprises reactive species, a pH buffer system, and solubilization ingredients,
said first part comprising:
stabilized hydrogen peroxide; and
an organic co-solvent;
said second part comprising:
a weak base aliphatic amine;
a phase transfer catalyst, said phase transfer catalyst comprising at least one quaternary ammonium compound;
a metal oxide catalyst; and
de-ionized water;
wherein said pH buffer system comprises said hydrogen peroxide, said weak base aliphatic amine, and said phase transfer catalyst;
wherein said solubilization ingredients comprise said organic co-solvent, said quaternary ammonium compound, and said weak base aliphatic amine; and
wherein said reactive species comprise a perhydrolysis species formed in reaction of said hydrogen peroxide with said weak base aliphatic amine, and a catalytic oxidative species formed in reaction of said hydrogen peroxide of the first part with said metal oxide catalyst.

20. The shelf-stable decontaminant composition of claim 19 wherein said hydrogen peroxide is stabilized by 0.1 mM to 20 mM of a phosphonate detergent.

21. The shelf-stable decontaminant composition of claim 19 wherein at least one of said first part and said second part is in the form of a concentrate.

22. The shelf-stable decontaminant composition of claim 19, wherein said first part and said second part are combined for use as a decontaminant no more than 6 hours before use at a temperature of about 20 degrees C. and no more than 24 hours before use at a temperature of about 0 degrees C.

23. The shelf-stable decontaminant composition of claim 19 that results from mixing said two parts comprising:
   about 15% hydrogen peroxide;
   about 4 mM phosphonate detergent;
   about 20% propylene glycol n-propyl ether;
   about 0.44 M N-benzylamine;
   about 1.50% hexadecyltrimethylammonium bromide;
   about 0.13 M tetrabutylammonium hydroxide;
   from about 1 mM to about 4 mM $MoO_4^=$;
   about 0.1 M sodium hydroxide; and
   a balance of de-ionized water.

* * * * *

UNITED STATES PATENT AND TRADEMARK OFFICE
CERTIFICATE OF CORRECTION

PATENT NO. : 7,776,362 B2  Page 1 of 1
APPLICATION NO. : 11/329531
DATED : August 17, 2010
INVENTOR(S) : Qian et al.

It is certified that error appears in the above-identified patent and that said Letters Patent is hereby corrected as shown below:

In Claim 8, "$^{32}$" should be deleted.

In Claim 9, "$^{32}$" should be deleted.

In Claim 10, "$^{32}$" should be deleted.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,776,362 B2                                                    Page 1 of 1
APPLICATION NO.   : 11/329531
DATED             : August 17, 2010
INVENTOR(S)       : Qian et al.

It is certified that error appears in the above-identified patent and that said Letters Patent is hereby corrected as shown below:

Column 18, line 4 (Claim 8, line 2) "$^{32}$" should be deleted.

Column 18, line 6 (Claim 9, line 2) "$^{32}$" should be deleted.

Column 18, line 8 (Claim 10, line 2) "$^{32}$" should be deleted.

This certificate supersedes the Certificate of Correction issued November 30, 2010.

Signed and Sealed this
Twenty-fifth Day of January, 2011

David J. Kappos
*Director of the United States Patent and Trademark Office*